（12） United States Patent
Abramowitz

(10) Patent No.: US 6,174,281 B1
(45) Date of Patent: Jan. 16, 2001

(54) LARYNGOSCOPE

(75) Inventor: Aron Abramowitz, Givat Zeev (IL)

(73) Assignee: Arcomedic Ltd., Omer (IL)

(*) Notice: Under 35 U.S.C. 154(b), the term of this patent shall be extended for 0 days.

(21) Appl. No.: 09/125,449

(22) PCT Filed: Dec. 25, 1996

(86) PCT No.: PCT/IL96/00191

§ 371 Date: Aug. 19, 1998

§ 102(e) Date: Aug. 19, 1998

(87) PCT Pub. No.: WO97/30626

PCT Pub. Date: Aug. 28, 1997

(30) Foreign Application Priority Data

Feb. 23, 1996 (IL) ........................................................ 117250

(51) Int. Cl.[7] .................................................... A61B 1/267
(52) U.S. Cl. ........................... 600/196; 600/194; 600/199; 600/131
(58) Field of Search .................................... 600/120, 131, 600/146, 185, 190, 194, 196, 199, 216

(56) References Cited

U.S. PATENT DOCUMENTS

| | | | | |
|---|---|---|---|---|
| 4,314,551 | * | 2/1982 | Kadell | 600/190 |
| 4,360,008 | * | 11/1982 | Corazelli et al. | 600/194 |
| 4,384,570 | * | 5/1983 | Roberts | 600/187 |
| 4,573,451 | * | 3/1986 | Bauman | 600/190 |
| 4,574,784 | * | 3/1986 | Soloway | 600/193 |
| 4,580,551 | * | 4/1986 | Siegmund et al. | 600/139 |
| 5,060,633 | * | 10/1991 | Gibson | 600/193 |
| 5,651,760 | * | 7/1997 | Upsher | 600/193 |

* cited by examiner

*Primary Examiner*—John P. Leubecker
(74) *Attorney, Agent, or Firm*—Nath & Associates; Gary M. Nath; Harold L. Novick

(57) ABSTRACT

An endotracheal inspection and intubation device comprising a handle and a blade, the blade comprising a rigid rear portion and a front portion with an intermediate flexible portion. The rear portion and the intermediate portion have a generally L-like cross-sectional shape with the front portion being essentially flat. The blade holds a flexible deflection member with a front end fixed to the front portion of the blade. The deflection member is slidably retained by guide means at least to the intermediate portion with a suitable activator for engaging with a rear end of the deflection member for causing axial displacement thereof, entailing deflection of the blade.

19 Claims, 8 Drawing Sheets

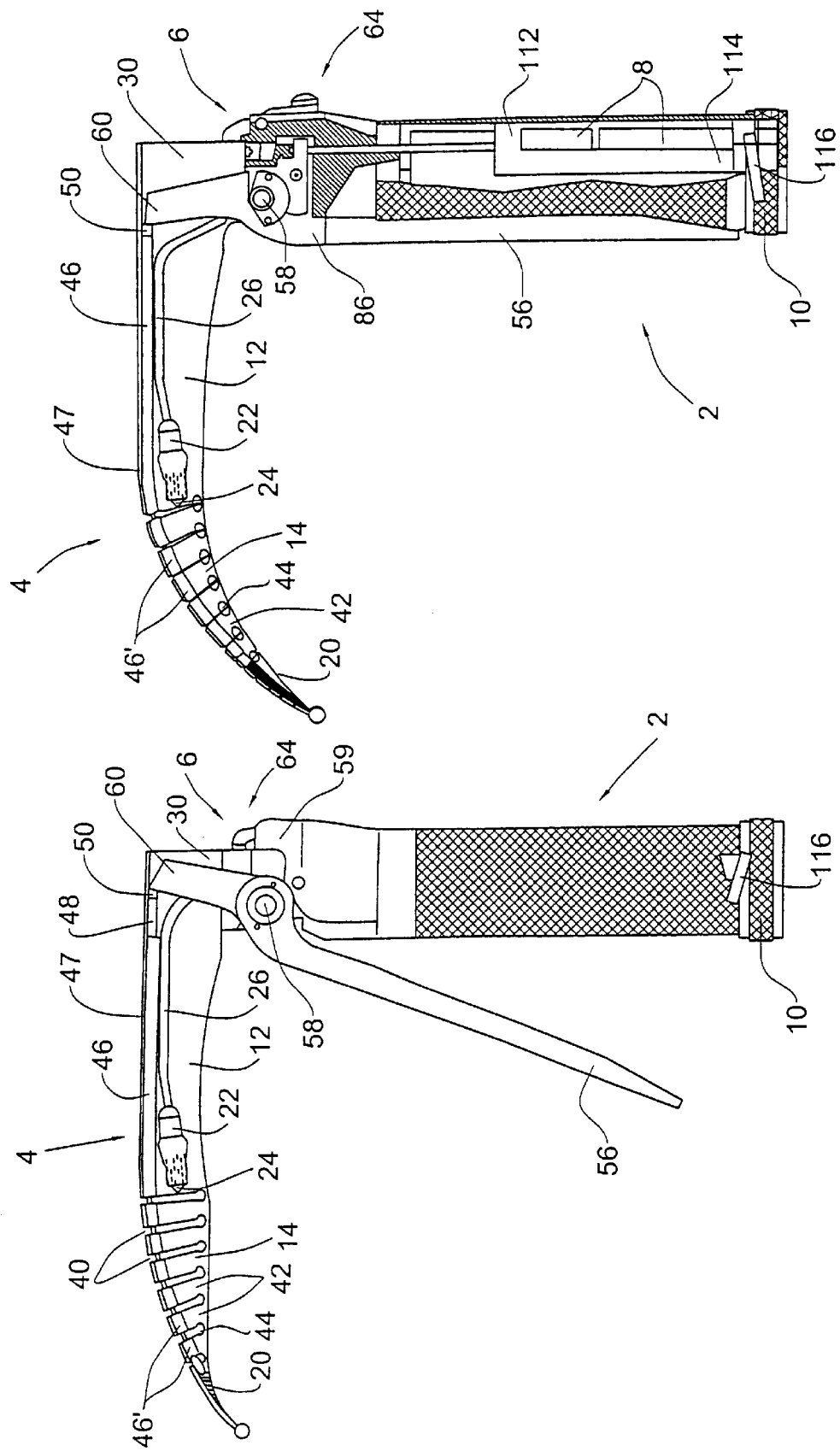

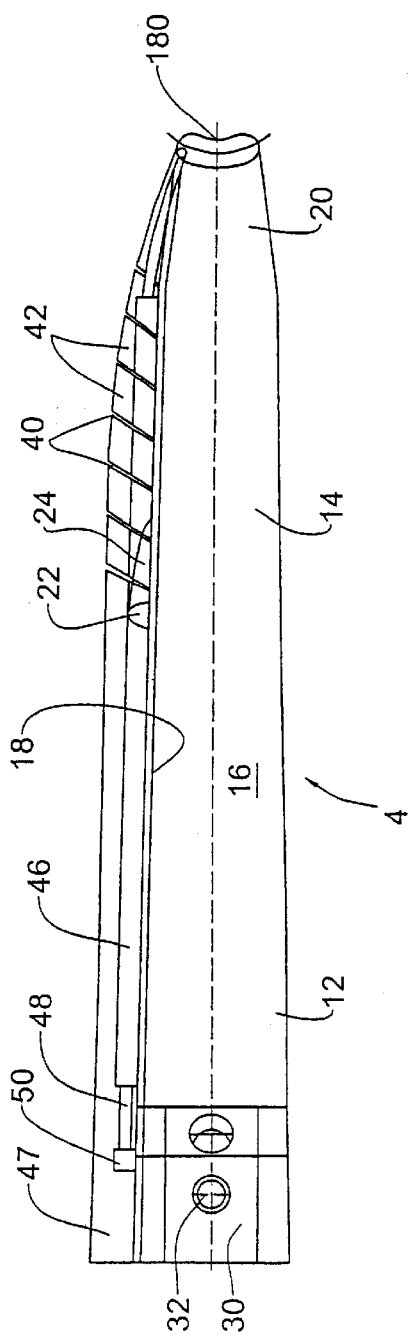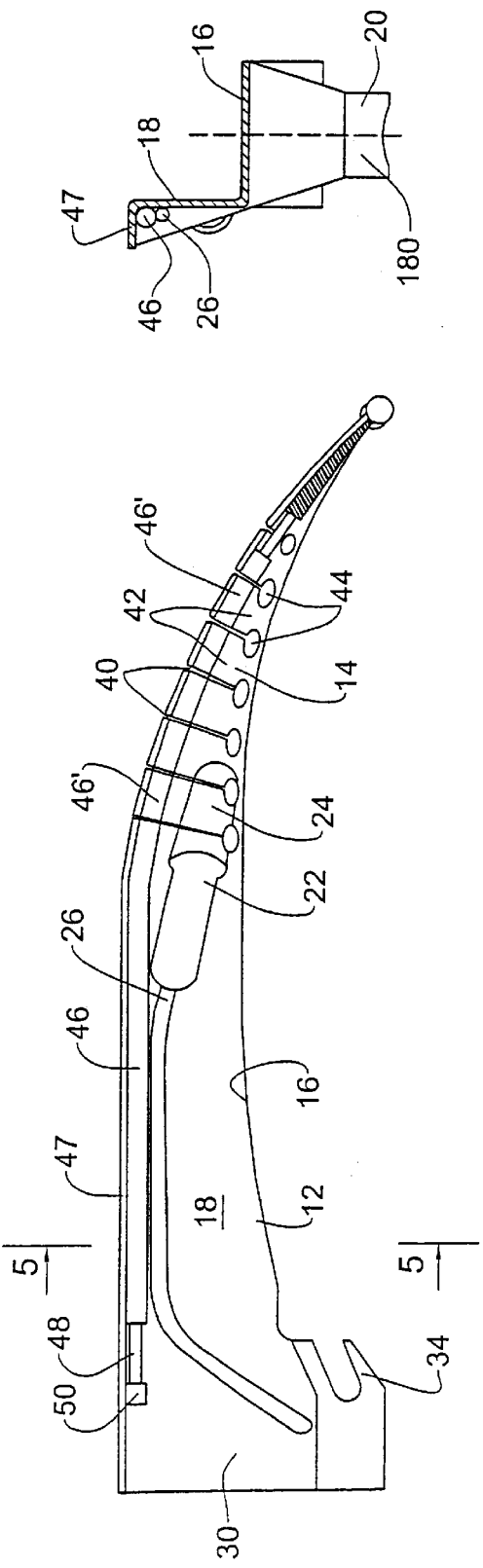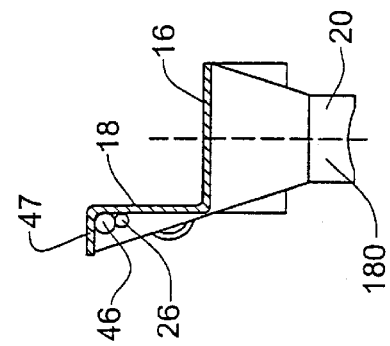

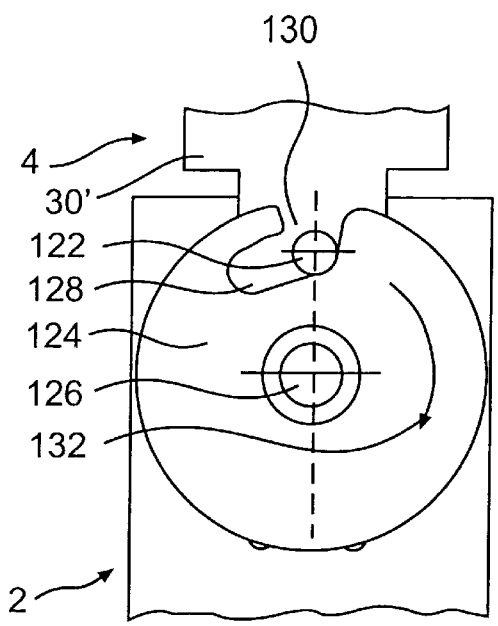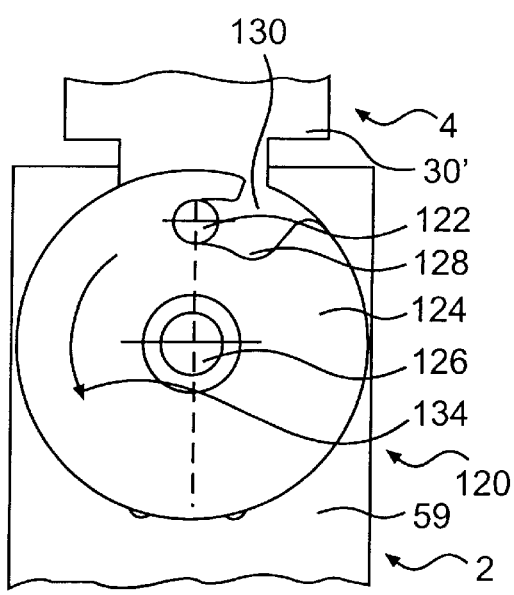
FIG. 9A  FIG. 9B
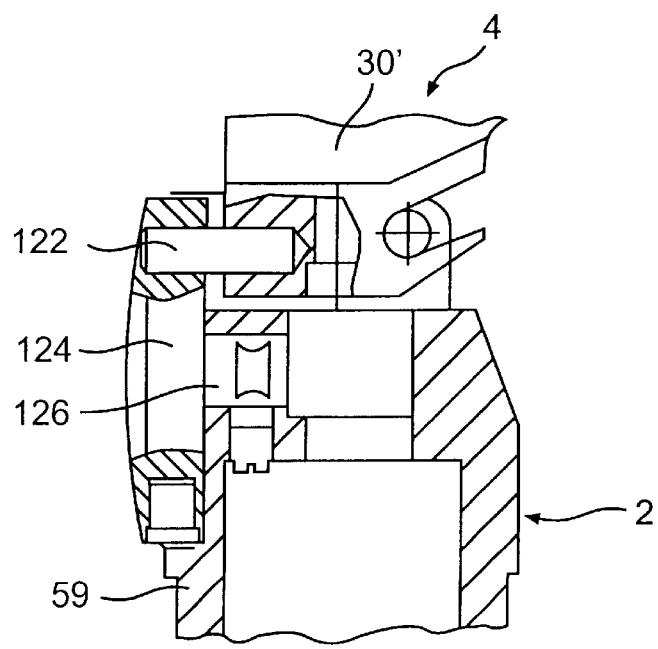
FIG. 9C

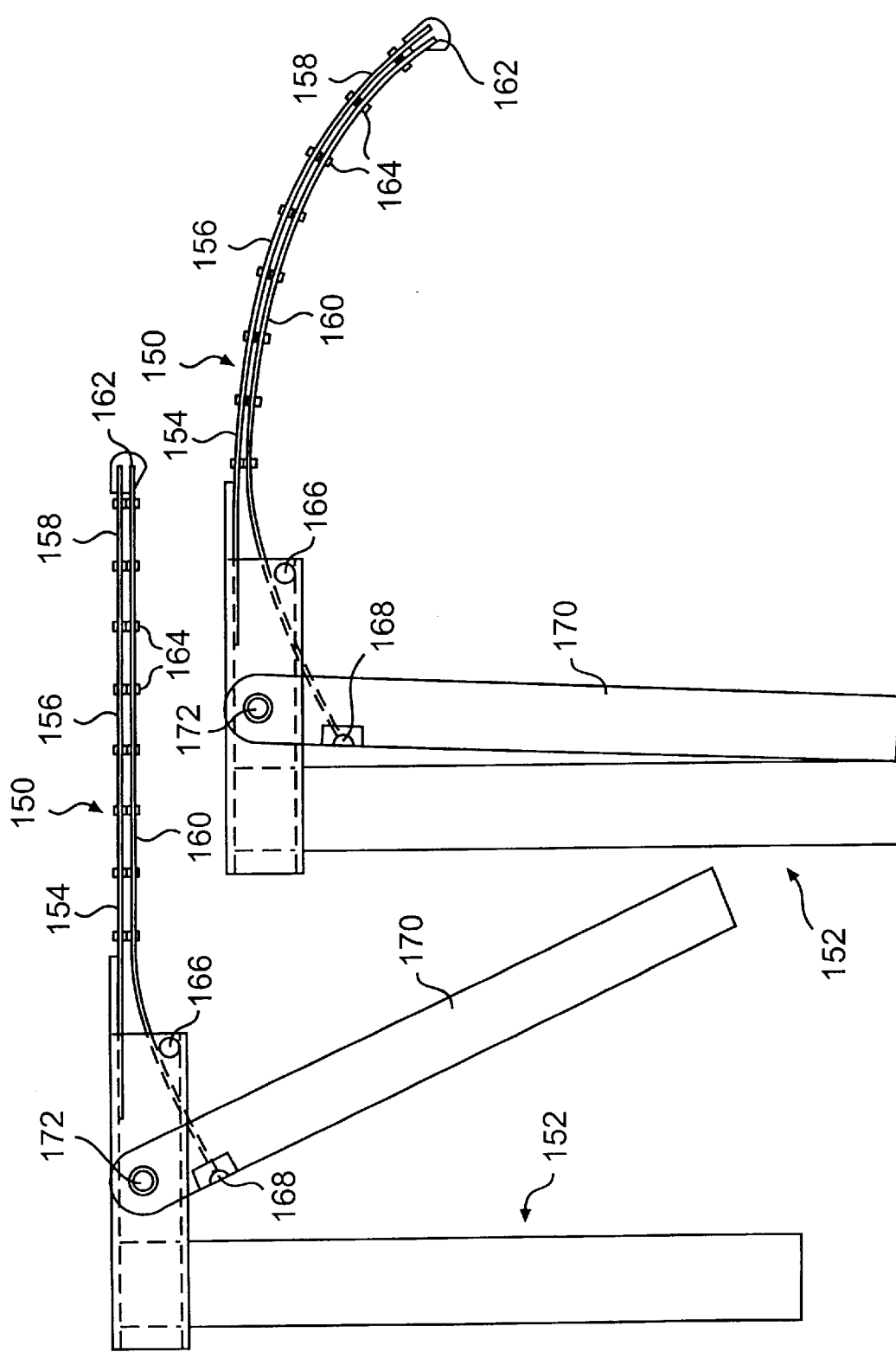

LARYNGOSCOPE

FIELD OF THE INVENTION

The present invention is in the field of medical equipment and more specifically it is concerned with a device for endotracheal inspection and intubation, referred to as a laryngoscope.

BACKGROUND OF THE INVENTION

Endotracheal inspection is required for visualizing the vocal cords and the opening to the trachea performed by physicians for many purposes. Endotracheal intubation wherein an airway tube is inserted into the trachea), is carried out at each general anaesthesia procedure and is a first and most crucial stage in resuscitation due to respiratory arrest. The intubation procedure must be performed as quickly and smoothly as possible and without injuring the patient.

Existing laryngoscopes require highly trained personnel for performing a correct intubation procedure and individual anatomic and physiologic parameters of each patient must be considered, e.g. tongue size, length of neck, variations of the lower jaw and teeth, etc., and even more so, special conditions such as spasm of neck and face muscles, head or neck injuries, etc.

The known laryngoscopes aye of standard sizes and shape and do not provide any adjusting to anatomic variants. In many cases, the blade of the laryngoscope losses grab of the tongue and slips out of position due to the oral mucosas, loosing fatal time and possibly injuring the patient.

It is an object of the present invention to provide a novel device for carrying out tracheal inspection and intubation procedures with essentially reducing the required level of skill for performing such procedures and reducing the probability of injury to patients.

SUMMARY OF THE INVENTION

According to the present invention there is provided an endotracheal inspection and intubation device comprising a handle and a blade for opening the trachea and allowing visualization of the vocal cords and the opening to the trachea, the blade holding an illuminator for illumination of the epiglottis and the opening to the trachea, with power source being comprised within the handle; the blade comprises a rigid rear and front portion and a flexible intermediate portion; the rear portion and the intermediate portion having a generally L-like cross-sectional shape with a horizontal base for depressing the tongue and a vertical member, the front end being essentially flat and having a shape and size such as to allow depression of the tongue's base and vallecula so as to elevate the epiglottis; the blade holding a flexible deflection member with a front end fixed to the front portion of the blade, the deflection member being slidably retained by guide means to at least the intermediate portion; the handle having an activator with an engagement member for engaging with a rear end of the deflection member for causing axial displacement thereof upon actuation of the activator, thus entailing deflection of the blade. The arrangement is such that the intermediate portion of the blade renders the blade inherent elasticity and adjustable bending force, whereby the blade tends to retain its original position.

According to a preferred embodiment of the present invention the vertical member in the intermediate portion is segmented by a plurality of slots, each of the slots having an open end at the members' top and extending downwards ending at the base; the blade holding a flexible pushing rod with a front end fixed to the front portion and a free rear end, the rod being slidably retained within guide means in the rear portion and in the upper end of the vertical member of each of the segments of the intermediate portion; the activator having a pushing member for bearing on to the free end and causing forward axial displacement of the pushing rod upon actuation of the activator.

By another embodiment of the present invention said deflection member is a cable fixed under the blade to the front end thereof and extending essentially flush with the blade's bottom surface by the guide means; said engagement member being a pulling member attached to a rear end of the cable for drawing the cable upon actuation of the activator.

According to a specific embodiment of the invention, the handle further comprises a ratchet mechanism activated by the activator for fixing the pushing member at intermediate positions, and a release mechanism for instant release of the ratchet mechanism. According to one variation, the final stroke of the ratchet mechanism is essentially longer than the preceding ones and said final stroke is not fixable.

According to one application, the ratchet mechanism comprises a cogged member fixed to the activator and rotatable about an axis of operation at a top end of the activator, and a swingable cogged pawl spring biased in a direction so as to arrest the cogged member at a desired angular position thereto and wherein the release mechanism consists of at least one knob projecting from the handle, said knob adjusted for displacing a prying rod for disengaging the cogged pawl of the ratchet mechanism form the cogged member.

The blade may be integral with the handle or, it may be detachably connected to the handle and secured thereto by a standard fitting. However, the handle may also be provided with an auxiliary locking device for rigidly connecting the blade to the handle.

A specific application of the auxiliary locking device comprises a pivotal, spring biased catch at a rear, top end of the handle being adapted for engagement within a suitable recess at a rear end of the blade. Another embodiment of the locking device may comprise said auxiliary locking device comprises a rotatable locking piece at a rear, top end of the handle, said locking piece provided with a groove having a peripheral opening and adapted for engaging a rearward projection of the blade.

In a preferred application of the preferred embodiment, each of the slots has at its end adjacent the base an opening for reducing stress concentration.

The blade according to the present invention may be made of a plastic or thermoplastic material and the front edge of the blade may have a tip concaved at a plane of the base or a tip convexed at a plane of the base. The tip may also be concaved at a plane perpendicular to that of the base.

BRIEF DESCRIPTION OF THE DRAWINGS

For better understanding, the invention will now be described by way of reference only, to the accompanying drawings, in which:

FIG. 1 is a side view of a laryngoscope according to a first embodiment of the present invention, the blade shown in its essentially flat position;

FIG. 2 is a partially sectioned side view of the laryngoscope according to the invention, the blade in its deflected position;

FIG. 3 is a bottom view of a blade for use with a laryngoscope according to the present invention;

FIG. 4 is a side view of the blade seen in FIG. 3;

FIG. 5 is a cross-section of the blade taken along line 5 in FIG. 4;

FIGS. 9a and 9b are rear views of a second embodiment of an auxiliary locking mechanism, in the unlocked and locked position, respectively;

FIG. 9c is a cross-sectional side view of the auxiliary locking mechanism of FIGS. 9a and 9b;

FIG. 10 is a schematic illustration of a laryngoscope according to a second embodiment of the present invention, the blade shown in its essentially flat position;

FIG. 11 is a schematic illustration of the laryngoscope of FIG. 10, the blade shown in its deflected position.

DETAILED DESCRIPTION OF PREFERRED EMBODIMENTS

Figure 6:
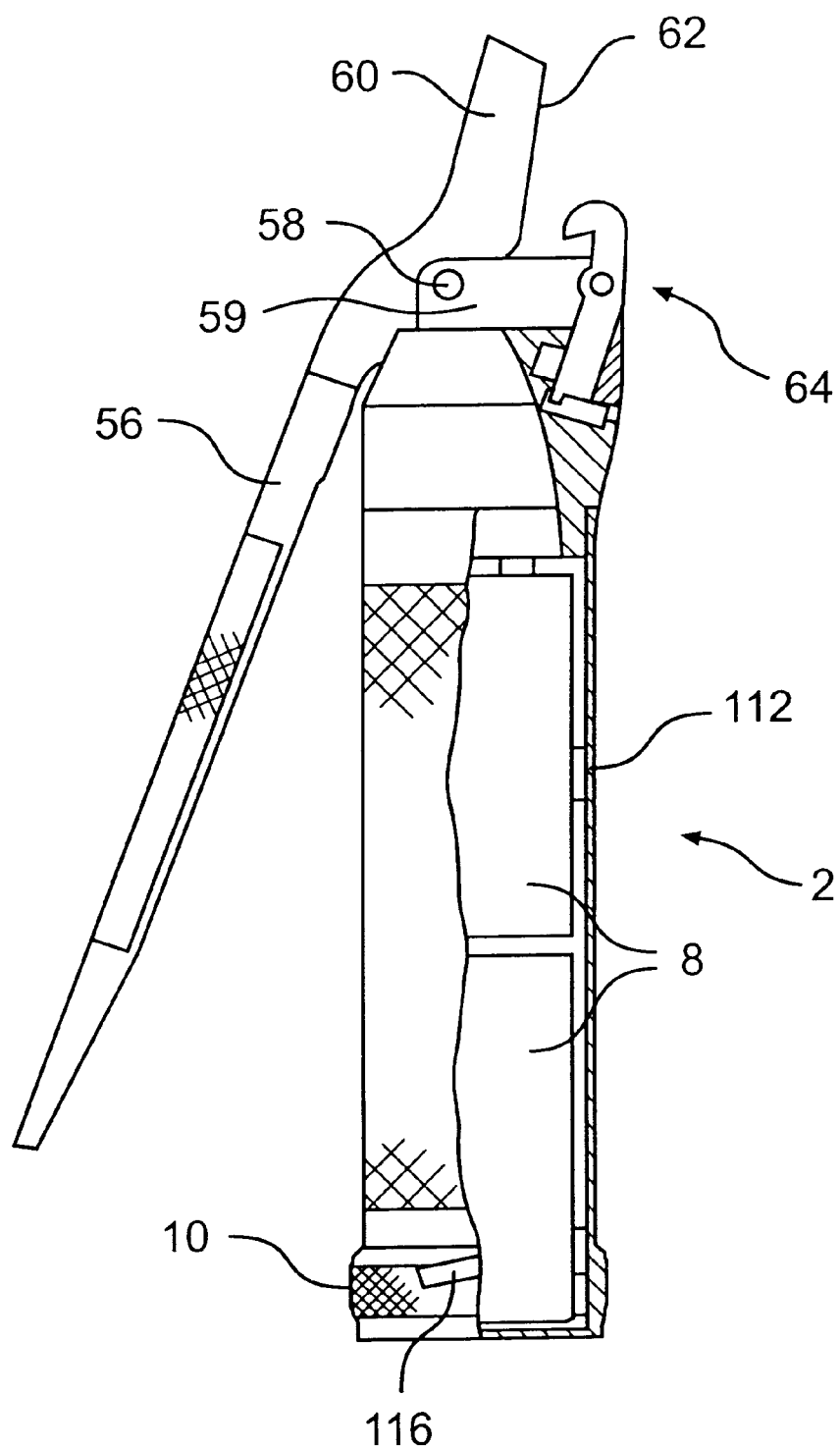
FIG. 6 is a side view of a handle for a laryngoscope according to the present invention.

Attention is first directed to FIGS. 1 and 2 of the drawings illustrating a laryngoscope according to the present invention assembled of a handle generally designated 2 and a blade generally designated 4 typically made of a heat treated surgical stainless-steel and being detachably connected to the handle at 6 by a standard ISO 7376 Fitting as known per se, allowing interchangeability with standard laryngoscope handles or blades.

As known in state of the art of laryngoscopes, the handle 2 accommodates two electric batteries 8 (seen only in FIG. 2) retained by a screw fitted cap 10 at a bottom end of the handle. As can better be seen in FIGS. 3 to 5, the blade 4 has a slightly curved longitudinal cross-section and has a rear portion 12 and an intermediate portion 14 having a generally L-like cross-sectional shape with an essentially horizontal flat base 16 and a vertical wall 18 and a front flat end 20.

The blade 4 is fitted with an illuminating bulb 22 fixed within a suitable indention 24 at the vertical wall 18 and an electric supply line 26 extending to the rear end 30 of the blade, provided with suitable electric contacts and a locking hook 34 for attaching to the handle 2 as known per se.

The intermediate portion 14 comprises a plurality of slots 40 dividing the intermediate portion into segments 42 and extending the entire length of the vertical wall 18, each slot terminating with an enlarged oval shaped opening 44 for reducing stress concentration as known per se, thus rendering the intermediate portion 14 flexible.

The blade 4 further comprises a guiding tube 46 fixed at the top of the vertical wall 18 by welding and extending along the rear and intermediate portions 12 and 14 respectively, the guiding tube 46 having segments 46' at the intermediate portion 14 in register with the segments 42 concealed by a top, essentially horizontal wall 47. A flexible pushing rod 48 is welded at a front end thereof to the front end 20 of the blade 4 and has a free rear end 50 projecting from the guide tube 46. The arrangement is such that the pushing rod 48 is slidable within the guiding tube 46, whereby forward axial displacement of the pushing rod 48 within the guiding tube 46 entails bending of the intermediate flexible portion 14, as seen in FIG. 2. The rate of bending depends on the amount of axial displacement of the pushing rod 48.

As can better be seen in FIG. 5 the handle 2 further comprises an actuating lever 56 pivoted at 58 to a top end 59 of the handle 2 between a released position (as seen in FIG. 1) and a compressed position (as seen in FIG. 2). The top end of the actuating lever has a pushing member 60 having a surface 62 for bearing on the free rear end 50 of the pushing rod 48 when the blade 4 is assembled on the handle 2.

The handle 2 further comprises at its top end 59 an auxiliary locking mechanism generally designated 64 for ensuring rigid and sturdy connection of the blade 4 to the handle 2. The auxiliary locking mechanism 64 is shown in more detail in FIGS. 7a and 7b in its unlocked and locked positions, respectively. The auxiliary locking mechanism consists of a catch 66 pivoted at 68 to the top end 59 of the handle 2 and is biased in a counter-clockwise direction by a compression spring 70 accommodated at its ends by suitable recesses 72 and 74 in the handle and catch respectively. The catch 66 has a hooked top end 76 engageable by a recess 78 at the rear locking end 30 of the blade 4.

Figure 7A:
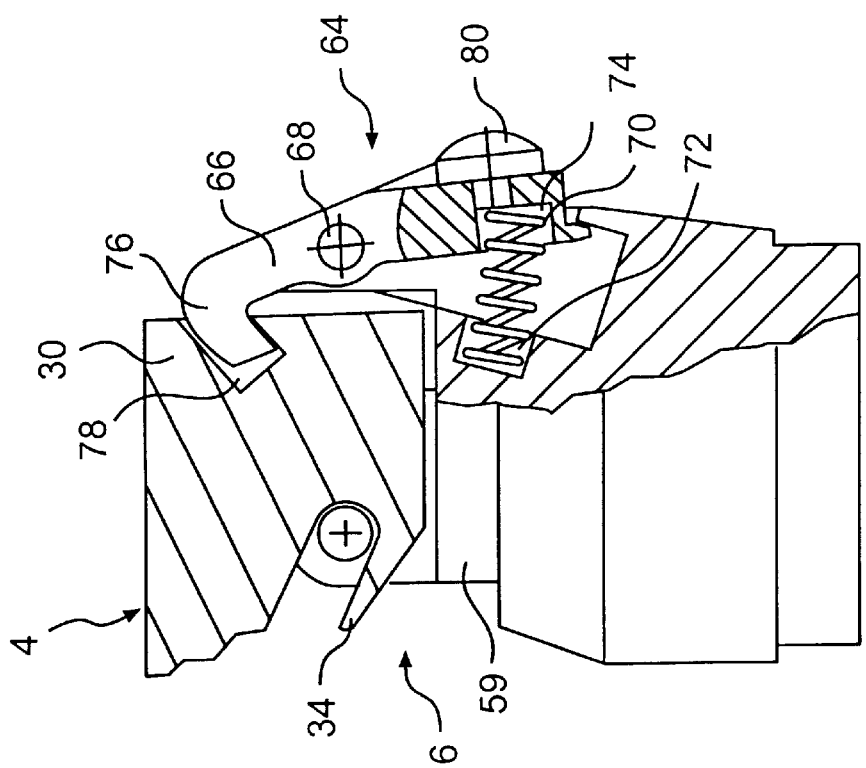
FIGS. 7a and 7b are partially sectioned views of the auxiliary locking mechanism of a laryngoscope according to the invention at an enlarged scale, in the disengaged and engaged position, respectively.
Figure 7B:
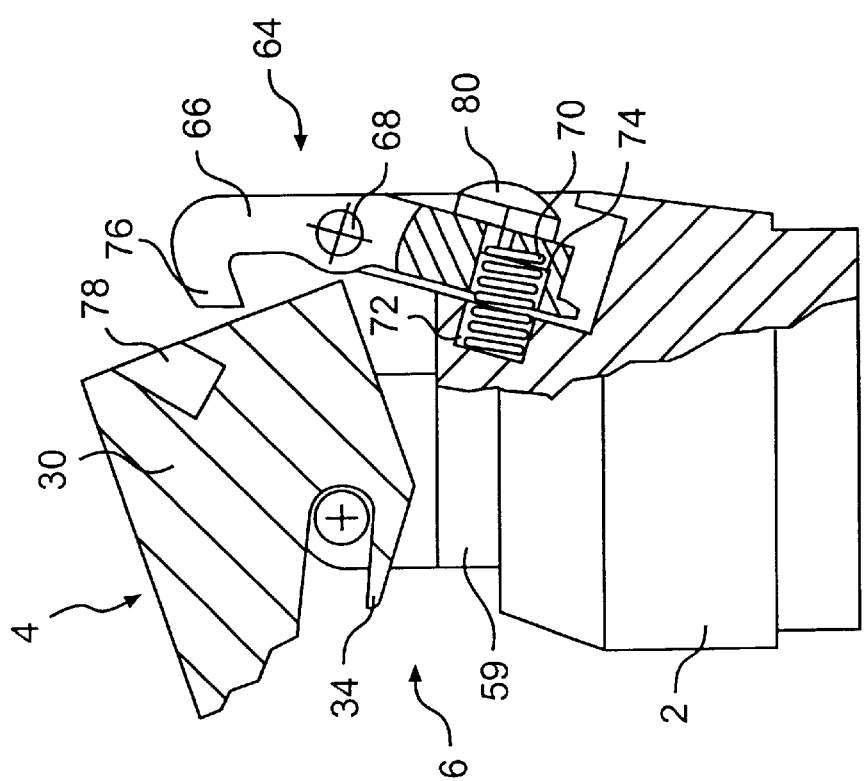

The arrangement is such that upon assembling the blade 4 to the handle 2 by means of the standard fitting at 6 (via locking hook 34 of blade 4) the catch 66 is first rotated to the position seen in FIG. 7a by the bottom edge of the rear locking end 30 encountering the catch and when the blade 4 is rotated into its final position as seen in FIG. 7b, the catch 66 pivotally snaps into its locking position with the hooked end 76 grabbing the handle 4 by the recess 78. Disconnecting the blade 4 from the handle 2 is performed in a reverse sequence of operation, i.e., first the catch 66 is pivoted in a clockwise direction by applying pressure on knob 80 (to the position shown in FIG. 7a) and then disconnecting the blade as known per se.

Figure 8A:
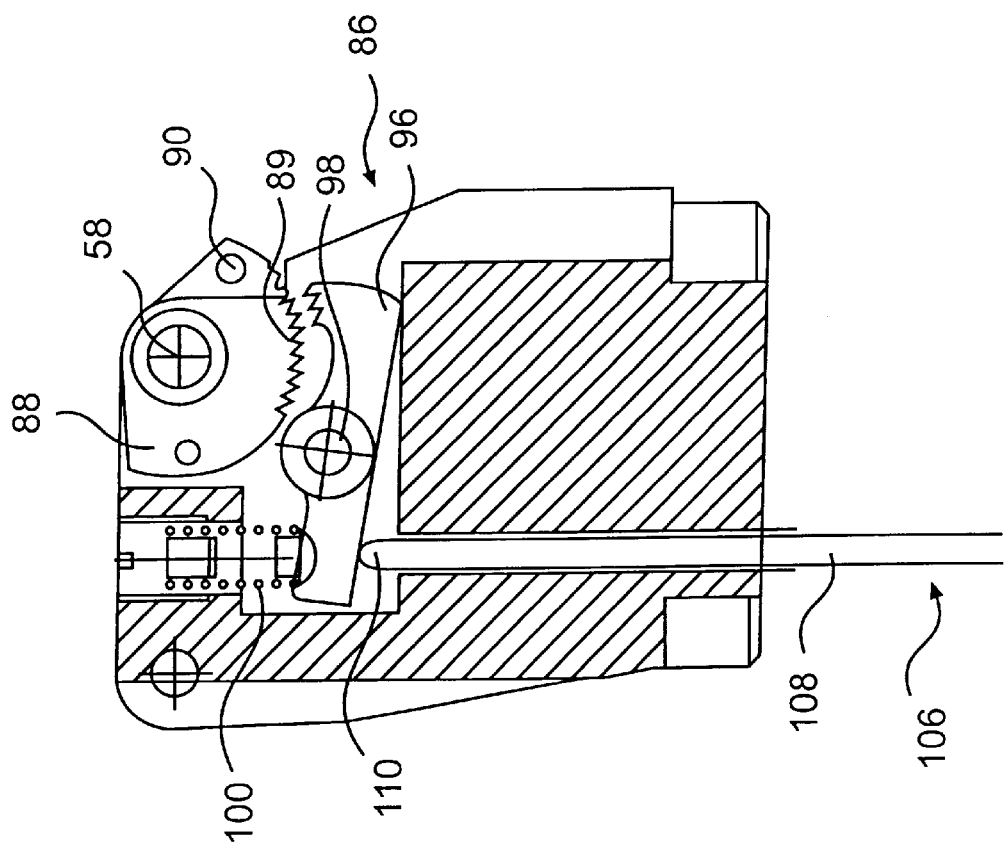
FIGS. 8a and 8b are cross-sectional views of the ratchet mechanism of a laryngoscope according to the invention at an enlarged scale, in the engaged and disengaged position, respectively.
Figure 8B:
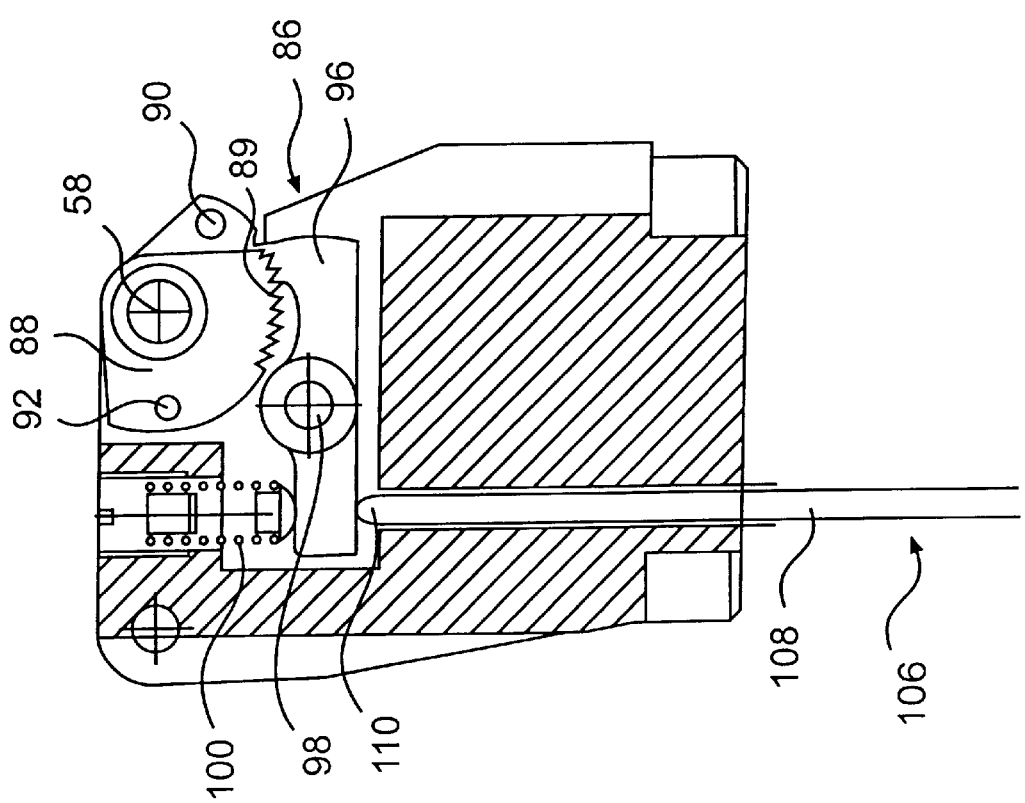

The handle 2 comprises also a ratchet mechanism generally designated at 86, illustrated in enlarged scale in FIGS. 8a and 8b in its engaged and disengaged positions, respectively. The purpose of the ratchet mechanism 86 is to fix the pushing member 60 of the activating lever 56 at variable angular positions for the reasons which will hereinafter be explained.

The ratchet mechanism 86 comprises a cogged member 88 having a shape of a circular sector with only a portion 89 of its perimeter being cogged, the cogged member being concentric with the pivot 58 of the actuating lever 56. Cogged member 88 is fixedly attached to the actuating lever 56 by screws at 92, whereby angular displacement of the actuating lever 56 entails angular displacement of the cogged member 88 in the same direction.

A cogged pawl 96 is suitably cogged at a first end so as to match the cogged portion of the cogged member 88 and is pivoted at 98 to the handle. The cogged pawl 96 is spring biased in a counter-clockwise direction by means of compression spring 100 received within an annular groove and bearing at a first end against a second end of the cogged pole 96 and at an opposed end against a top wall within the handle. The arrangement is such that the cogged pawl 96 is normally engaged with the cogged member 88 and angular displacement of the latter is irreversible unless the cogged pawl 96 is disengaged from the cogged member by a release mechanism 106 as will hereinafter be explained.

As can be seen in FIGS. 2,6 and 8 of the drawings, the release mechanism 106 consists of a rod 108 having its top end 110 bearing against the rear end of the cogged pawl 96, opposite the biasing spring 100. The opposed end of the rod 108 is linked to a bar 112, having two arms 114 (only one of which is seen in FIG. 2). The arms 114 extend flush with the inner wall of the handle 2 and each arm has at its end a knob 116 laterally projecting from the handle.

The arrangement is such that normally the release mechanism 106 is downwardly retracted by the biasing effect of the compression spring 100. However, exerting light force on either of the knobs 116 displaces the rod 108 in a direction against the biasing effect of the spring 100, as a result of which the cogged pawl 96 is caused to pivot in a clockwise direction, thus disengaging from the cogged member 88 and allowing spontaneous return of the latter to its original position as shown in FIG. 1, owing to elasticity of the blade.

FIGS. 9a to 9c illustrate a different embodiment of an auxiliary locking mechanism 120 according to which the rear locking end 30' of the blade 4 has a rearward projecting pin 122. A locking disk 124 is rotatably mounted at 126 to the top end 59 of the handle 2. The locking disk 124 comprises a groove 128 extending along an annular sector of the disk and having a peripheral opening 130.

For locking the auxiliary locking mechanism 120, the disk 124 is so positioned with the opening 130 receiving the projecting pin 122 and then the disk is rotated in a clockwise direction as of arrow 132 in FIG. 9A, whereby pin 122 becomes engaged by the groove 128. For releasing the auxiliary locking mechanism 120, the disk 124 is rotated in a counter-clockwise direction as of arrow 134 in FIG. 9b.

Reference is now made to FIGS. 10 and 11 of the drawings schematically illustrating a second embodiment of a laryngoscope according to the present invention, wherein a blade 150 is connected to a handle 152, the blade having a rigid rear portion 154, a flexible intermediate portion 156 and a rigid front end 158.

A flexible cable 160 is fixedly attached at 162 to the front end 158 of the blade and extends rearwardly under the blade 150 supported thereto by hooks 164 enabling axial displacement of the cable 160. The rear end of the cable 160 passes over a guide member 166 and is attached at 168 to an actuating lever 170 pivoted at 172 to the handle 152.

The arrangement is such that upon pulling the actuating lever 170, the cable 160 is retracted, causing deflection of the blade 150 as seen in FIG. 11, whereby releasing the actuating lever 170 entails spontaneous return of the blade 150 and the actuating lever 170 to the original position of FIG. 10, owing to the elasticity of the blade 150.

It should be realized to a person versed in the art that similar applications described with reference to the first embodiment, e.g. ratchet mechanism, release mechanism, etc. may also be applied on a device according to the second embodiment of the invention.

Attention is now directed back to FIGS. 3 and 5 in which it is seen that the tip 180 of the blade 4 is concave in a plane of the base 16 (seen in FIG. 3) and preferably also in the plane perpendicular to the plane of the base 16 of the blade 4 (seen in FIG. 5). This shape of the tip 180 of the blade better conforms with the anatomic shape of the tongue and the opening to the trachea. However, for neonates and premature infants, it may be required to use a blade having a tip convexed at the plane of the blade (not shown).

It should further be understood that different sizes of blades may be used as known in the art, e,g, blades ranking in size from 0 to 3. Even more so, blades of different arcs may be used for different anatomic abnormalities.

Figure 13:
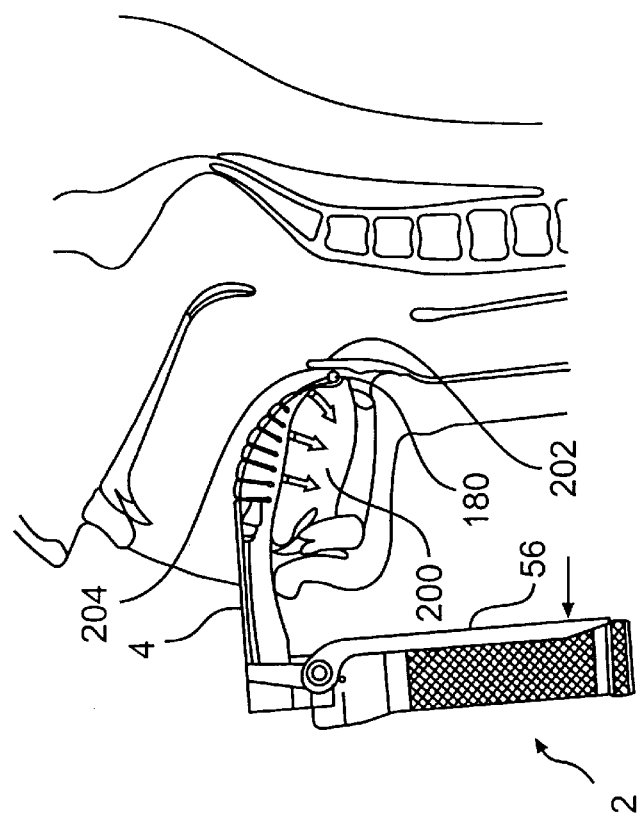
FIGS. 12 and 13 are sagittal sections illustrating performing a laryngoscopy with a laryngoscope according to the present invention.
Figure 12:
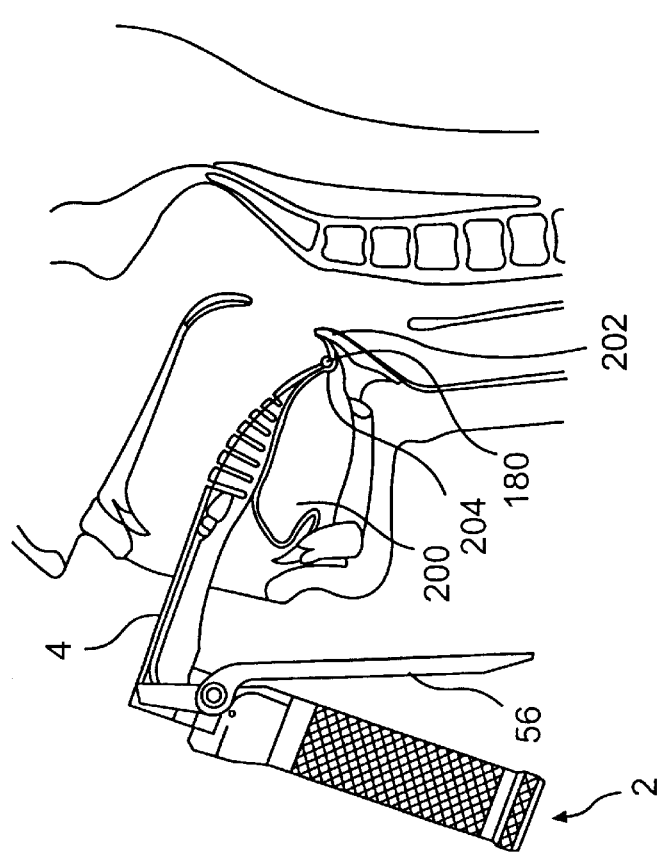

Attention is now directed to FIGS. 12 and 13 for understanding how the laryngoscope according to the invention is actually used. The laryngoscope should be gripped firmly by the operator's hand and the blade 4 is inserted from the right side of the mouth, gently lifting and sweeping the tongue 200 to the left, visualizing the larynx. The curved blade is slowly advanced along the base of the tongue 200 until the epiglottis 202 is visualized. The tip 180 of the blade is inserted into the space between the base of the tongue 200 and the epiglottis 202 (the vallecula 204). The operator's wrist is then fixed in position and further exposure is then gained by gently pulling at the activating lever 56, slowly bending the blade 4 without loss of rigidity along the blade. Owing to the ratchet mechanism, the bent position of the blade is fixed at any desired position or may rapidly be released by the release mechanism 106, by knobs 116 as hereinabove explained. Manipulating the blades' arc enables dynamic change of the configuration of the blade during the insertion of the laryngoscope and in accordance with the congruency to the relevant anatomical structures. At the final and critical stage of the manipulation, the movement of the activator enables "bio-feedback control" by the operator, wherein the blade may be further deflected or released as felt by the operator, allowing further improvement of visualization of the opening to the trachea without trauma or complications.

It should be realized that in a heretofore known laryngoscope, the visualizing of the trachea is obtained by fixing the operator's wrist and lifting the laryngoscope vertically forward while applying moment, which in many cases leads to slippage of the blade over the tongue (due to tongue mucosas). However, according to the present invention, visualization of the trachea is obtained merely by manipulating the actuating lever 56.

What is claimed is:

1. An endotracheal inspection and intubation device comprising a handle and a blade for opening the trachea and allowing visualization of the vocal cords and the opening to the trachea, the blade holding an illuminator for illumination of the epiglottis and the opening to the trachea, with power source being comprised within the handle;

the blade comprises a rigid rear and front portion and a flexible intermediate portion;

the rear portion and the intermediate portion having a generally L-like cross-sectional shape with a horizontal base for depressing the tongue and a vertical member, the front portion being essentially flat and having a shape and size such as to allow depression of the tongue's base and vallecula so as to elevate the epiglottis;

the blade holding a flexible deflection member with a front end fixed to the front portion of the blade, the deflection member being slidably retained by guide means to at least the intermediate portion;

the handle having an activator with an engagement member for engaging with a rear end of the deflection member for causing axial displacement thereof upon actuation of the activator, thus entailing deflection of the blade; and wherein the vertical member in the intermediate portion is segmented by a plurality of slots, each slot of said plurality of slots having an open end and a closed end, whereby each of said open ends is disposed at the vertical member's top edge, each of said slots extending downwards therefrom towards a bottom edge of said vertical member and ending at corresponding closed ends, wherein each of said closed ends of said plurality of slots comprises a region having a larger cross-sectional area.

2. An endotracheal inspection and intubation device according to claim 1, wherein the flexible deflecting member is a flexible pushing rod with a front end fixed to the front portion and a free rear end, the rod being slidably retained within guide means in the rear portion and in the upper end of the vertical member of each of the segments of the intermediate portion; the activator having a pushing member for bearing on to the free rear end and causing forward axial displacement of the pushing rod upon actuation of the activator.

3. An endotracheal inspection and intubation device according to claim 2, wherein the handle further comprises a ratchet mechanism activated by the activator for fixing the pushing member at intermediate positions, and a release mechanism for instant release of the ratchet mechanism.

4. An endotracheal inspection and intubation device according to claim 3, wherein a final stroke of the ratchet mechanism is essentially longer than the preceding ones.

5. An endotracheal inspection and intubation device according to claim 4, wherein the final stroke is not fixable.

6. An endotracheal inspection and intubation device according to claim 3, wherein the ratchet mechanism comprises a cogged member fixed to the activator and rotatable about an axis of operation at a top end of the activator, and a swingable cogged pawl spring biased in a direction so as to arrest the cogged member at a desired angular position thereof.

7. An endotracheal inspection and intubation device according to claim 6, wherein the release mechanism consists of at least one knob projecting from the handle, said knob adjusted for displacing a prying rod for disengaging the cogged pawl of the ratchet mechanism from the cogged member.

8. An endotracheal inspection and intubation device according to claim 1, wherein the handle and blade are integral with one another.

9. An endotracheal inspection and intubation device according to claim 1, wherein the blade is detachably connected to the handle and secured thereto by a standard fitting.

10. An endotracheal inspection and intubation device according to claim 9, wherein the handle is provided with an auxiliary locking device for rigidly connecting the blade to the handle.

11. An endotracheal inspection and intubation device according to claim 10, wherein said auxiliary locking device comprises a pivotal, spring biased catch at a rear, top end of the handle being adapted for engagement within a suitable recess at a rear end of the blade.

12. An endotracheal inspection and intubation device according to claim 10, wherein said auxiliary locking device comprises a rotatable locking piece at a rear, top end of the handle, said locking piece provided with a groove having a peripheral opening and adapted for engaging a rearward projection of the blade.

13. An endotracheal inspection and intubation device according to claim 1, wherein the blade is made of plastic material.

14. An endotracheal inspection and intubation device according to claim 1, wherein the front portion of the blade has a tip concaved at a plane of the base.

15. An endotracheal inspection and intubation device according to claim 1, wherein the front portion of the blade has a tip concaved at a plane perpendicular to that of the base.

16. An endotracheal inspection and intubation device according to claim 1, wherein the front portion of the blade has a tip convexed at a plane of the base.

17. An endotracheal inspection and intubation device according to claim 1, wherein said deflection member is a cable fixed under the blade to the front end thereof and extending essentially flush with the blade's bottom surface by the guide means; said engagement member being a pulling member attached to a rear end of the cable for drawing the cable upon actuation of the activator.

18. An endotracheal inspection and intubation device according to claim 1 wherein said enlarged opening has an oval shape.

19. An endotracheal inspection and intubation device according to claim 1, wherein said region of said closed ends of said slot having a larger cross-sectional area extends to said horizontal base of said intermediate portion of said blade.

* * * * *